United States Patent [19]

Thakur et al.

[11] Patent Number: 5,134,108
[45] Date of Patent: Jul. 28, 1992

[54] PROCESS FOR PREPARING CATALYST WITH COPPER OR ZINC AND WITH CHROMIUM, MOLYBDENUM, TUNGSTEN, OR VANADIUM, AND PRODUCT THEREOF

[75] Inventors: Deepak S. Thakur, Solon; Eugene Palka, Parma; Thomas J. Sullivan, Strongsville; Eugene Nebesh, Parma; Brian D. Roberts, Cleveland Heights, all of Ohio

[73] Assignee: Engelhard Corporation, Edison, N.J.

[21] Appl. No.: 703,923

[22] Filed: May 22, 1991

[51] Int. Cl.$^5$ .................. B01J 37/03; B01J 23/22; B01J 23/06; B01J 23/24

[52] U.S. Cl. .................. 502/318; 502/307; 502/343; 502/345; 502/306; 502/315; 502/316; 502/324; 502/329; 502/328; 502/337; 502/338; 502/340; 502/331

[58] Field of Search .............. 502/318, 307, 343, 345, 502/306, 315, 316, 324, 329, 328, 337, 338, 340, 331

[56] References Cited

U.S. PATENT DOCUMENTS

| | | | |
|---|---|---|---|
| 2,091,800 | 8/1937 | Adkins et al. | 260/156 |
| 2,121,367 | 6/1938 | Schiller | 260/156 |
| 2,782,243 | 2/1957 | Hess et al. | 260/638 |
| 3,173,959 | 3/1965 | Rittmeister | 260/638 |
| 3,267,157 | 8/1966 | Miya | 260/638 |
| 3,385,448 | 5/1968 | Honan et al. | 210/407 |
| 3,697,605 | 10/1972 | Watanabe et al. | 502/306 |
| 3,894,054 | 7/1975 | Miya | 260/346.1 R |
| 3,971,735 | 7/1976 | Asano et al. | 252/432 |
| 4,113,662 | 9/1978 | Wall | 502/329 |
| 4,279,781 | 7/1981 | Dienes et al. | 252/46 |
| 4,291,126 | 9/1981 | Sugier et al. | 518/713 |
| 4,440,668 | 4/1984 | Chang et al. | 502/331 |
| 4,513,100 | 4/1985 | Fattore et al. | 502/303 |
| 4,535,071 | 8/1985 | Schneider et al. | 502/342 |
| 4,551,444 | 11/1985 | Lin et al. | 502/313 |
| 4,598,061 | 7/1986 | Schneider et al. | 502/303 |
| 4,675,343 | 6/1987 | Courty et al. | 518/713 |
| 4,704,480 | 11/1987 | Gepri et al. | 568/396 |
| 4,808,562 | 2/1989 | Kubersky | 502/172 |
| 5,030,609 | 7/1991 | Turner et al. | 502/318 |

FOREIGN PATENT DOCUMENTS

| | | | |
|---|---|---|---|
| 1178045 | 9/1964 | Fed. Rep. of Germany | 502/318 |
| 57-123127 | 7/1982 | Japan | 502/318 |
| 1436773 | 5/1976 | United Kingdom . | |

*Primary Examiner*—W. J. Shine
*Assistant Examiner*—Douglas J. McGinty
*Attorney, Agent, or Firm*—Renner, Otto, Boisselle & Sklar

[57] ABSTRACT

This hydrogenation catalyst comprises a major amount of the oxides of a first metal selected from copper or zinc, a second metal selected from chromium, molybdenum, tungsten and vanadium, and optionally, a minor amount of the oxide of a promoter metal selected from the group consisting of manganese, barium, zinc, nickel, cobalt, cadmium, iron and any combination thereof provided that the promotor metal is not zinc if the first metal is zinc. The average particle diameter of the powder is from about 6 to about 20 microns; and the particle surface area is from about 20 to about 70 m$^2$/g. The process for preparing this catalyst comprises the steps of (A) simultaneously and adding to a first vessel, (1) a first aqueous solution comprising a copper or zinc salt; (2) a second aqueous solution comprising a soluble base, provided that either the copper solution or the soluble base solution also contains a soluble salt of at least one second metal; or (3) a third aqueous solution comprising a soluble salt of at least one seocnd metal is added simultaneously to the first vessel whereby an aqueous slurry of insoluble solid is formed in the first vessel, provided further that the second metal is chromium, molybdenum, tungsten, or vanadium;

(B) advancing at least a portion of the aqueous slurry from the first vessel to a second vessel;

(C) recovering the solids from the aqueous slurry in the second vessel; and (D) calcining the recovered solids.

32 Claims, No Drawings

PROCESS FOR PREPARING CATALYST WITH COPPER OR ZINC AND WITH CHROMIUM, MOLYBDENUM, TUNGSTEN, OR VANADIUM, AND PRODUCT THEREOF

TECHNICAL FIELD

This invention relates to catalysts which are particularly useful as hydrogenation catalysts, and more particularly, catalysts for hydrogenating aldehydes, ketones, carboxylic acids and carboxylic esters. The invention also relates to a method of preparing said catalysts and to the use of the catalysts in hydrogenation reactions.

BACKGROUND OF THE INVENTION

In one embodiment, the present invention relates to catalysts which are useful in hydrogenation reactions and which comprise the oxides of copper or zinc and at least one other metal. The preparation of various copper-containing catalysts and the use of such catalysts in various reactions has been described previously. Such reactions include hydrogenation reactions, the synthesis of methanol and higher alcohols from synthesis gas, etc. The copper-containing catalysts also may contain other metal oxides including chromium oxide, zinc oxide, titanium oxide, zirconium oxide, iron oxide, alumina, silica, etc., and mixtures of one or more of said oxides.

The hydrogenation of carboxylic acids and carboxylic esters to alcohols is known in the art, and various methods and catalysts have been suggested for effecting the hydrogenation reaction. For example, the ester may be reduced with lithium aluminum hydride or sodium and alcohol. A commonly practiced method involves the use of a copper-chromite-based hydrogenation catalyst.

U.S. Pat. No. 2,091,800 describes a copper chromite/barium catalyst which is used in a process for hydrogenating esters at a temperature in the range of 200° C. to 400° C. by passing the acid and its esters over the hydrogenation catalyst. U.S. Pat. No. 2,285,448 describes the preparation of polyhydric alcohols such as ethylene glycol from esters of glycolic acid using a hydrogenation catalyst. Fused metal oxide catalysts are prepared and copper oxide catalysts are described. Copper oxide catalyst containing other metal oxides such as the oxides of magnesium, nickel, iron, cobalt, manganese, chromium, calcium, barium, strontium, potassium, calcium, zinc, cadmium, silver, or mixtures thereof, are described as useful. The specific examples of the hydrogenation reaction uses a copper-magnesium oxide catalyst. Other patents describing various types of copper chromite catalysts used in acid and ester hydrogenation processes include U.S. Pat. Nos. 2,121,367; 2,782,243; 3,173,959; and 3,267,157.

U.S. Pat. No. 3,894,054 describes the production of tetrahydrofuran by catalytic hydrogenation and dehydration of maleic anhydride using a catalyst composition which comprises a mixture obtained by calcining a silica-alumina catalyst and a copper-chromium-zinc catalyst. U.S. Pat. No. 3,971,735 describes the preparation of methanol from syngas with a catalyst comprised of copper, zinc, aluminum and boron. The hydrogenation of esters to alcohols by contacting the ester with hydrogen and a catalyst comprising cobalt, zinc and copper under catalytic hydrogenation conditions is described in U.S. Pat. No. 4,113,662. U.S. Pat. No. 4,279,781 describes a methanol synthesis catalyst which comprises the oxides of copper and zinc and a minor amount of a thermal stabilizing metal oxide such as alumina. The copper to zinc metal-weight ratio is in the range of from 2:1 to 3.5:1. Catalysts comprising copper, cobalt, a metal selected from chromium, iron, vanadium or manganese, a rare earth metal and a small amount of an alkali or alkaline earth metal are described in U.S. Pat. No. 4,291,126. Optionally, the catalyst may contain zinc and/or a noble metal and/or a binder selected from alumina, magnesia and cements. U.S. Pat. No. 4,440,668 describes a three-component oxide catalyst based on copper, a metal from Group VIA, VIIA or VIIIA, and a metal of Group IVA or VA. The preferred catalyst is based on copper, cobalt and zirconium with the first two components being formed by co-precipitation in the presence of the oxide of the third component. Another multi-component catalytic system is described in U.S. Pat. No. 4,513,100 which comprises zinc, chromium, copper, one or more alkaline metals and possibly one or more metals chosen from molybdenum, manganese, lanthanum, cerium, aluminum, titanium and vanadium.

U.S. Pat. No. 4,535,071 describes a catalyst for methanol synthesis from syngas which comprises as catalytically active substances, copper oxide and zinc oxide and as a thermal stabilizing substance, aluminum oxide. Optimum yields of methanol are obtained when the atomic ratio of copper to zinc is between 2.8 and 3.8. Five-component catalyst compositions are described in U.S. Pat. No. 4,551,444 and the essential components are copper, an iron group component, a component of elements 23-26, an alkaline metal compound and a precious metal compound. Catalysts comprising copper oxide and zinc oxide in a ratio of 8:1 to 1:1 are described in U.S. Pat. No. 4,588,848 as being useful in synthesizing neoalcohols from neoacids. U.S. Pat. No. 4,598,061 describes a catalyst for synthesis of methanol and alcohol mixtures from synthesis gas using a catalyst which contains, as an oxide precursor, copper oxide and zinc oxide; aluminum oxide as a thermal stabilizing substance; and at least one alkali metal compound. Catalysts comprising copper and cobalt, and optionally aluminum and/or zinc and/or sodium are utilized in U.S. Pat. No. 4,675,343 for preparing primary aliphatic alcohols from hydrogen and carbon oxides. The catalysts contain a minimum of 3% cobalt. Catalysts containing the oxides of copper, zinc and alumina are described in U.S. Pat. No. 4,704,480 as being useful in the production of aliphatic ketones and an optional consecutive production of the corresponding carbinols. More specifically, catalysts comprising the oxides of copper, zinc and alumina are utilized in Examples 1 and 11 of the patent and a catalyst comprising the oxides of copper and alumina is utilized in Example 12. Copper-zinc catalysts also are described in U.S. Pat. No. 4,808,562, and the catalysts may contain alumina.

U.K. Patent 1,436,773 also describes copper oxide, zinc oxide catalysts obtained by coprecipitation which are suitable for use in the synthesis of methanol from synthesis gas. The ratio of copper to zinc in the catalyst is from 1:1 to 8:1, and the catalyst may contain a thermal stabilizer such as alumina. Japanese Patent 62-53740 apparently describes catalysts derived from the nitrates of copper, zinc, manganese/magnesium and aluminum.

German Offenlegungschrift 2,613,226 describes a continuous preparation of fatty alcohols by catalytic hydrogenation of relatively high molecular weight fatty acids and esters formed with low-molecular weight monohydric alcohols. The process utilizes hydrogen and a catalyst. The catalysts disclosed in the patent include copper chromite or copper-zinc-chromite and copper-zinc catalysts with or without known carrier substances.

Although many copper-containing catalysts have been described in the prior art, there continues to be a need for catalysts which are useful particularly in the hydrogenation of aldehydes, acids and esters, including diesters. It is also desirable to prepare catalysts useful in hydrogenation reactions which can be carried out in either a fixed bed or a fluidized bed reactor.

SUMMARY OF THE INVENTION

In one embodiment, the invention relates to a catalyst which comprises a major amount of the oxides of a first metal selected from copper and zinc, and a second metal selected from chromium, molybdenum, tungsten and vanadium. Optionally the catalysts also comprise a minor amount of the oxide of a promoter metal selected from the group consisting of manganese, barium, zinc, nickel, cobalt, cadmium, iron and any combination thereof provided the promoter metal is not zinc when the first metal is zinc. The catalysts are characterized as having a relatively narrow particle size distribution and a relatively narrow pore volume distribution. The average particle diameter of the powder catalysts of the invention is from about 6 to about 20 microns, and the particle surface area is from about 20 to about 70 m$^2$/g. In another embodiment, the invention relates to a process for preparing hydrogenation catalysts comprising the oxides of copper or zinc and at least one additional metal which comprises the steps of (A) simultaneously and separately adding to a first vessel, (1) a first aqueous solution comprising a copper or zinc salt; and (2) a second aqueous solution comprising a soluble base, provided that either the first or second solution also contains a soluble salt of at least one second metal; or (3) a third aqueous solution comprising a soluble salt of at least one second metal is added simultaneously to the first vessel whereby an aqueous slurry of an insoluble solid is formed in the first vessel, provided further that the second metal is chromium, molybdenum, tungsten, or vanadium;

(B) advancing at least a portion of the aqueous slurry from the first vessel to a second vessel;

(C) recovering the solids from the aqueous slurry in the second vessel; and (D) calcining the recovered solids. The invention also relates to a process for hydrogenating aldehydes, ketones, carboxylic acids and carboxylic acid esters with catalysts of the type described. Catalysts of the invention are useful in both fixed bed and slurry phase hydrogenation reactions.

DESCRIPTION OF THE PREFERRED EMBODIMENTS

In one embodiment, the present invention relates to a powder catalyst comprising a major amount of the oxides of a first metal selected from the group of copper and zinc, a second metal selected from chromium, molybdenum, tungsten and vanadium, and optionally, a minor amount of the oxide of a promoter metal selected from the group consisting of manganese, barium, zinc, nickel, cobalt, cadmium, iron and any combination thereof provided that the promoter metal is not zinc if the first metal is zinc. The average particle diameter of the powder is from about 6 to about 20 microns, and the particle BET specific surface area is from about 20 to about 70 m$^2$/g. In one preferred embodiment, the pore volume of the pores having a diameter in the range of about 120 to about 350 Å is from about 40 to about 80% of the total pore volume. All references to pore diameters and pore volumes in the specification and claims are based upon measurements of particles utilizing mercury porosimetry. A typical method is described by R. Anderson, *Experimental Methods in Catalytic Research*, Academic Press, N.Y., 1968. The pore volumes are determined utilizing the powder forms of the catalysts in their oxide forms. That is, the pore diameters reported herein are obtained for the powder catalyst after calcination, but prior to any reduction of the oxide. Those skilled in the art often refer to the catalyst containing the metal oxides as the "oxide" or "oxidic precursor" form of the catalyst even though not all of the metal is in the oxide form. It should also be understood that the metals may be present in different valence states.

The powdered catalysts of the present invention are characterized as having a low average surface area of from about 20 to about 70 square meters per gram and more generally from about 25 to about 65 square meters per gram. The powdered catalysts also may be characterized as having an average particle diameter of from about 6 to about 12 microns. The catalysts of the invention also are characterized by narrow particle size and pore size distributions. For example, in one embodiment, the particles are all below 25 microns in diameter, at least about 80% of the particles are below 15 microns, about 50% are 8 microns or less, and about 0% is below 2 microns.

In one embodiment, the pore volume of pores of the catalyst having a diameter in the range of from about 120 to about 350 Å is from about 40 to about 80% of the total pore volume. The pore volume of pores having a diameter in the range of up to about 120 Å is from about 5 to about 45% of the total pore volume, and the pore volume of pores having a diameter of from about 350 to about 1000 Å is from about 10 to about 40% of the total pore volume.

The packed apparent bulk density of the catalysts ranges from about 0.8 to about 1.3 g/cc.

The first metal may be zinc or copper. Copper is a preferred first metal. In addition to copper or zinc, the catalysts of the present invention will contain at least one other metal including a second metal selected from the group consisting of chromium, molybdenum, tungsten and vanadium. In one preferred embodiment, the second metal is chromium. The catalysts of the present invention may be characterized as having a copper or zinc to second metal atomic ratio of from about 0.8 to about 1.2. In other embodiments, the atomic ratio of copper to second metal (e.g., chromium) is about 1.

In addition to the oxides of copper or zinc, and the above-described second metals, the catalysts of the present invention may, and preferably do contain oxides of at least one promoter metal selected from the group consisting of manganese, barium, zinc, nickel, cobalt, cadmium and iron. Of the above-described promoter metals, manganese is particularly preferred. The amount of promoter metal present in the catalyst of the present invention may be any amount from 0 to about 15% by weight based on the total weight of metals in the catalysts. In one preferred embodiment, the catalysts of the present invention will contain from 1 to about 15% by weight of the promoter metal. Manganese contents of about 3 to about 10% or from about 3 to about 5% and barium contents of from about 6 to about 10% by weight have been found to be particularly useful when either of these metals are incorporated into the powdered catalysts of the present invention.

Various procedures can be utilized to prepare the copper catalysts of the present invention. For example, individual aqueous solutions of copper or zinc and each of the other metals may be prepared and mixed together followed by the addition of an aqueous alkaline solution. Alternatively, a first aqueous solution comprising a copper or zinc salt and a second aqueous solution comprising a soluble base and at least one soluble salt of at least one second metal can be prepared, and these two solutions are then added simultaneously to a vessel containing water. When the promoter metal is to be included in the catalyst composition of the present invention, a water-soluble salt of the promoter metal may be included in either the first aqueous solution or the second aqueous solutions described above, or a fourth aqueous solution containing a water-soluble salt of a promoter metal may be prepared and simultaneously mixed with the first and third aqueous solutions described above, or the first, second and third solutions described above. In any of the above embodiments which may be considered to be batch processes, aqueous slurries are formed in the vessels and the solids are recovered from the slurries. As described below, the catalysts can also be prepared by semi-continuous or continuous processes. Calcination of the recovered solids does not have to be effected in a continuous manner. The recovered solids can be accumulated and stored for subsequent calcination at an appropriate or convenient time.

One embodiment of the present invention relates to a preferred process for preparing catalysts of the invention comprising the oxides of copper or zinc and at least one additional metal, and this preferred process (semi-continuous) comprises the steps of (A) simultaneously and continuously adding to a first vessel, (1) a first aqueous solution comprising a copper or zinc salt; and (2) a second aqueous solution comprising a soluble base, provided that either the first or second solution also contains a soluble salt of at least one second metal selected from the group consisting of chromium, molybdenum, tungsten, or vanadium; or (3) a third aqueous solution comprising a soluble salt of at least one second metal is added simultaneously to the first vessel whereby an aqueous slurry of an insoluble solid is formed in the first vessel.

(B) advancing at least a portion of the aqueous slurry from the first vessel to a second vessel;

(C) recovering the solids from the aqueous slurry in the second vessel; and (D) calcining the recovered solids.

In addition to the above aqueous solutions, water may be added separately and simultaneously to the first vessel as the first and second solutions are added. If water is added separately, the amount of water in the first and second solutions can be reduced.

When it is desired to incorporate at least one promoter metal into the copper catalysts of the present invention, a water-soluble salt of at least one promoter metal selected from the group consisting of manganese, barium, zinc, nickel, cobalt, cadmium, iron, calcium, magnesium, and any combination thereof may be included in the first aqueous solution or in the third aqueous solution, if a third aqueous solution is utilized. Alternatively, a fourth aqueous solution of a water-soluble salt of the promoter metal is prepared and added simultaneously to the first vessel in step (A).

In one preferred embodiment, the soluble second metal salt is included in the first aqueous solution. When a promoter metal is to be incorporated into the catalyst of the present invention, the water-soluble salt of the promoter metal is preferably included in the first aqueous solution, and thus, the first aqueous solution in this embodiment will comprise the soluble salts of copper (or zinc), the second metal, and the promoter metal.

In another embodiment, the process of the present invention involves a process which comprises the steps of (A) simultaneously and continuously adding to a first vessel: water; a first aqueous solution comprising soluble salts of copper, a second metal selected from the group consisting of chromium, molybdenum, tungsten or vanadium, and a promoter metal selected from the group consisting of manganese, barium, zinc, nickel, cobalt, cadmium, iron and any combination thereof, provided that the promoter metal is not zinc; and a second aqueous solution comprising a soluble base, to form an aqueous slurry of an insoluble solid in the first vessel;

(B) continuously advancing at least a portion of the aqueous slurry from the first vessel to the second vessel;

(C) recovering at least some of the solid from the slurry in the second vessel; and (D) calcining the recovered solid. In yet another embodiment, the formation and recovery of the solids can be a continuous process wherein in step (C) the solids are continuously removed and recovered from the slurry in the second vessel as the solids accumulate. It has been observed that when the process of the present invention is utilized in the formation of the copper or zinc catalysts of the present invention, the catalysts generally are characterized by: narrow particle size distribution; narrow pore size distribution; low bulk density; more spherical particles; and when reduced, the catalysts exhibit a high copper or zinc concentration on the surface. It has also been observed that when the catalysts are used in slurry or ebulated bed reactors, filtration rates are improved. It is believed that the novel characteristics of the copper or zinc catalysts of the present invention result at least in part from the continuous nature of the process of the present invention. As noted above, the aqueous solution or solutions containing water-soluble salts of the desired metals, the aqueous solution comprising a soluble base and, optionally, water are added simultaneously and continuously to a reaction vessel whereby an aqueous slurry of an insoluble solid is formed in the first vessel. The residence time in the first vessel may be varied and will depend on a number of factors such as the apparatus, particular reactants, reaction rates, concentration of reactants, etc. Temperature is not critical. Temperatures of from 10° to 95° C. and more generally 10° to 60° C. may be used. Ambient temperature is common. Generally, the conditions are controlled to result in the preparation of the catalyst having the desired characteristics and properties. For example, an increase in the residence time within the first vessel will result in an increase in particle size.

At least a portion of the aqueous slurry formed in the first vessel is removed to a second vessel where the solids are recovered from the aqueous slurry. Any technique for recovering the solids from the aqueous slurry contained in a second vessel can be utilized such as by sedimentation, filtration, centrifugation, etc.

The solids which are recovered may be washed with water to remove impurities, and/or dried by heating to a temperature up to about 150° C. The solids recovered in this manner are finally calcined at a desirable temperature such as temperatures in the range of from about 350° C. to about 500° C. Time for calcination may be varied over a wide range, and will depend, in part, on the amount of powder calcined and the temperature of the calcination. Generally, at temperatures of from about 350° C. to about 500° C., calcination is completed in a period of from about 10 to about 120 minutes. In one embodiment, calcination at a temperature of about 400°–500° C. for about 10 minutes to one hour is sufficient. When the calcination is conducted at the lower end of this temperature range, e.g., 400°–425° C., the particles obtained have generally higher surface areas than the particles obtained by calcinating at higher temperatures such as 450°–460° C.

The water-soluble copper or zinc, and other metal salts utilized to form the aqueous solutions used in the present invention are salts such as the nitrates, acetates, sulfates, chlorides, etc. When the second metal is chromium, chromic acid or ammonium chromate may be utilized. It is presently preferred to use the nitrates of copper or zinc, and the nitrates of the various other metals other than chromium.

The soluble bases which are utilized to prepare the second aqueous solution may be soluble bases such as ammonium hydroxide, ammonium carbonate, ammonium chromate, etc., and mixtures thereof. Chromiums containing less ammonium chromate also are a source of desirable chromium metal. Mixtures of sodium hydroxide or carbonate and soluble ammonium salts such a ammonium chloride, etc. may be used as the soluble base. The amount of soluble base included in the second solution may be varied over a wide range, and the amount of the soluble base should be sufficient to provide an alkaline solution which, added to the reaction vessel, will result in a mixture having the desired pH. The pH of the mixture obtained by mixing the first and second solutions (and any other solutions of the type described above) should be within the range of about 4.5 to about 7 and more generally is from about 5 to about 6.5. The pH of the ultimate mixture can be maintained as desired by adjusting the addition of the various solutions. The mixture or aqueous slurry formed in the reaction vessel upon the addition and mixing of the various solutions is generally at about ambient temperature.

The following examples illustrate various embodiments of the present invention for preparing the powdered copper catalysts of the present invention. Unless otherwise indicated in the examples and elsewhere in the specification and claims, all parts and percentages are by weight, temperatures are in degrees Centigrade and pressures are at or near atmospheric.

EXAMPLE 1

A first solution (Solution A) is prepared from 1200 parts of an aqueous copper nitrate solution containing 16.3% copper, 143 parts of an aqueous manganese nitrate solution containing 15% manganese, 337 parts of chromic acid and 1150 parts of water. A second solution (Solution B) is prepared by dissolving 674 parts of concentrated ammonium hydroxide (29% as $NH_3$) in 230 parts of water. The first and second solutions are added slowly and simultaneously with vigorous agitation along with a third stream (C) of water to a reactor vessel (or an in-line mixer) which is connected to a larger holding vessel to allow effluent from the reactor to pass to the holding vessel. The reaction pH and temperature are maintained at 6.0° and 27° C. respectively. The ratio of flow rates of solution (A+B) to water (C) is 1:1. A precipitate is formed and recovered from the slurry in the holding vessel by filtration and washed with water. The residue is dried at about 130° C., and the dried material is then calcined at 415°–425° C. for 10 minutes. The calcined product is the desired catalyst containing, by analysis, 36.8 wt. % copper, 32.1 wt. % chromium, and 3.5 wt. % manganese. The average particle size of the calcined product is about 10 microns.

EXAMPLE 2

A first solution (Solution A) is prepared from 1200 parts of an aqueous copper nitrate solution containing 16.3% copper, 143 parts of an aqueous manganese nitrate solution containing 15% manganese, 337 parts of chromium trioxide and 1150 parts of water. The second solution (Solution B) is prepared by dissolving 674 parts of concentrated ammonium hydroxide (29% as $NH_3$) in 230 parts of water. The first and second solutions are added slowly and simultaneously with vigorous agitation along with a third stream (C) of water to a reactor vessel (or an in-line mixer) which is connected to a larger holding vessel to allow effluent from the reactor to pass to the holding vessel. The reaction pH and temperature are maintained at 6.0° and 27° C. respectively. The ratio of flow rates of solution (A+B) to water (C) is 1:1.5. A precipitate is formed and recovered from the slurry in the holding vessel by filtration and washed with water. The residue is dried at about 130° C., and the dried material is then calcined at 415°–425° C. for 10 minutes. The average particle size of the calcined product is about 8.5 microns.

EXAMPLE 3

A first solution (Solution A) is prepared from 1200 parts of an aqueous copper nitrate solution containing 16.3% copper, 143 parts of an aqueous manganese nitrate solution containing 15% manganese, 337 parts of chromium trioxide and 1150 parts of water. The second solution (Solution B) is prepared by dissolving 674 parts of concentrated ammonium hydroxide (29% as $NH_3$) in 230 parts of water. The first and second solutions are added slowly and simultaneously with vigorous agitation along with a third stream (C) of water to a reactor vessel (or an in-line mixer) which is connected to a larger holding vessel to allow effluent from the reactor to pass to the holding vessel. The reaction pH and temperature are maintainaed at 6.0° and 27° C. respectively. The ratio of flow rates of solution (A+B) to water (C) is 1:2.5. A precipitate is formed and recovered from the slurry in the holding vessel by filtration and washed with water. The residue is dried at about 130° C., and the dried material is then calcined at 415°–425° C. for 10 minutes. The average particle size of the calcined product is about 7.0 microns.

EXAMPLE 4

A first solution (Solution A) is prepared from 1200 parts of an aqueous copper nitrate solution containing 16.4% copper, 143 parts of an aqueous manganese nitrate solution containing 15% manganese, 337 parts of chromium trioxide and 1150 parts of water. The second solution (Solution B) is prepared by dissolving 674 parts of concentrated ammonium hydroxide (29% as $NH_3$) in 230 parts of water. The first and second solutions are added slowly and simultaneously with vigorous agitation along with a third stream (C) of water to a reactor vessel (or an in-line mixer) which is connected to a larger holding vessel to allow effluent from the reactor to pass to the holding vessel. The reaction pH and temperature are maintained at 5.2° and 27° C. respectively. The ratio of flow rates of solution (A+B) to water (C) is 1:1.5. A precipitate is formed and recovered from the slurry in the holding vessel by filtration and washed with water. The residue is dried at about 130° C., and the dried material is then calcined at 415°–425° C. for 10 minutes. The average particle size of the calcined product is about 10 microns.

EXAMPLE 5

A first solution (Solution A) is prepared from 1200 parts of an aqueous copper nitrate solution containing 16.3% copper, 143 parts of an aqueous manganese nitrate solution containing 15% manganese, 337 parts of chromium trioxide and 1150 parts of water. The second solution (Solution B) is prepared by dissolving 674 parts of concentrated ammonium hydroxide (29% as $NH_3$) in 230 parts of water. The first and second solutions are added slowly and simultaneously with vigorous agitation along with a third stream (C) of water to a reactor vessel (or an in-line mixer) which is connected to a larger holding vessel to allow effluent from the reactor to pass to the holding vessel. The reaction pH and temperature are maintained at 6.0° and 27° C. respectively. The ratio of flow rates of solution (A+B) to water (C) is 1:5. A precipitate is formed and recovered from the slurry in the holding vessel by filtration and washed with water. The residue is dried at about 130° C., and the dried material is then calcined at 415°–425° C. for 10 minutes. The calcined product is the desired oxide catalyst containing, by analysis, 38.7 wt. % copper, 30.3 wt. % chromium and 3.5 wt. % manganese. The average particle size of the calcined product is about 7 microns.

EXAMPLE 6

A first solution (Solution A) is prepared from 1200 parts of an aqueous copper nitrate solution containing 16.3% copper, 143 parts of an aqueous manganese nitrate solution containing 15% manganese, 337 parts of chromium trioxide and 1150 parts of water. The second solution (Solution B) is prepared by dissolving 674 parts of concentrated ammonium hydroxide (29% as $NH_3$) in 230 parts of water. The first and second solutions are added slowly and simultaneously with vigorous agitation along with a third stream (C) of water to a reactor vessel (or an in-line mixer) which is connected to a larger holding vessel to allow effluent from the reactor to pass to the holding vessel. The reaction pH and temperature are maintained at 6.0° and 27° C. respectively. The ratio of flow rates of solution (A+B) to water (C) is 1:1.5. A precipitate is formed and recovered from the slurry in the holding vessel by filtration and washed with water. The residue is dried at about 130° C., and the dried material is then calcined at 450°–460° C. for 10 minutes. The average particle size of the calcined product is about 8.5 microns.

Typical characteristics and properties of calcined compositions prepared in accordance with the general procedures of Examples 1–5 and the procedure of Example 6 are summarized in Table I and Table II.

TABLE I

|  | Ex. 1-5 | Ex. 6 |
|---|---|---|
| Surface area (m²/g) | 61 | 44 |
| He Density (g/cc) | 5.2 | 5.2 |
| Hg Density (g/cc) |  |  |
| at 18.5 psi | 1.2 | 1.4 |
| at 175 psi | 1.8 | 1.7 |
| at 1750 psi | 2.4 | 2.5 |

TABLE II

| Pore Size Distribution* | Pore Volume Distribution | | | | | |
|---|---|---|---|---|---|---|
|  | Ex. 1-5 | | | Ex. 6 | | |
|  | cc/g | % PV | Cum % PV** | cc/g | % PV | Cum % PV** |
| <60 | 0.0047 | 2.27 |  | 0.0289 | 12.66 |  |
| 60–90 | 0.0053 | 2.56 |  | 0.0022 | 0.96 |  |
| 90–120 | 0.0131 | 6.33 | 11.16 | 0.0041 | 1.8 | 15.42 |
| 120–200 | 0.075 | 36.27 |  | 0.0339 | 14.86 |  |
| 200–350 | 0.063 | 30.42 | 66.69 | 0.097 | 42.51 | 57.37 |
| 350–600 | 0.0211 | 10.2 |  | 0.0323 | 14.15 |  |
| 600–1000 | 0.0247 | 11.94 | 22.11 | 0.0298 | 13.06 | 27.21 |

*Å diameter
**for combination of ranges indicated

The powdered catalysts of the present invention may be utilized in slurry- (liquid-) phase hydrogenation processes. Alternatively, the powders can be processed into shapes such as pellets and used in fixed bed reactors. In one embodiment, carboxylic acids and carboxylic esters can be converted to alcohols in excellent yields. A wide variety of acids, particularly esters of carboxylic acids can be treated with the catalyst of the present invention to produce alcohols. The esters may be monoesters or diesters. Among the acids which may be hydrogenated to the corresponding alcohols without isolating the ester include stearic acids and caproic acids. Examples of esters which may be hydrogenated with the catalyst of the present invention include the methyl ester of coconut fatty acid, methyl stearate, methyl oleate, ethyl laurate, ethyl myristate, the diethyl ester of ethyl malonic acid, diethyl succinate, di-n-butyl glutarate, di-ethyl sebacate and dimethyl ester of terephthalic acid. As noted, the esters are converted to alcohols, and examples of such conversions include: ethyl laurate to lauryl alcohol; ethyl myristate to myristyl alcohol; ethyl valerate to n-amyl alcohol; methyl caproate to n-hexyl alcohol, etc.

Examples of aldehydes which may be hydrogenated with the catalyst of the present invention include: butyraldehyde, furfural, 2-ethyl-hexanal, dodecanal, tetradecanal, etc. Examples of ketones include acetone, acetophenone, etc.

The hydrogenation reactions which are conducted in the presence of the catalyst of the present invention are carried out at temperatures of from about 250° C. to about 350° C. and at pressures of from about 1500 psi to about 4500 psi.

In one preferred embodiment, the hydrogenation reaction is conducted in a batch reactor or continuously ebullated bed reactor. In this process, the catalyst powder particles are slurried with the aldehyde, ketone, carboxylic acid or carboxylic ester to be reduced, and there is intimate contact between the catalyst and the liquid. When the preferred catalysts of the present invention containing an atomic ratio of Cu:Cr of about 1:1, and the catalyst is prepared by the preferred simultaneous and continuous precipitation procedure such as illustrated in Examples 1-6, is used in a batch ebullated reactor, high yields of alcohols are obtained in shorter times. Also, the slurry, upon completion of the hydrogenation reaction is easily filtered.

A process for hydrogenating a diester is illustrated as follows. The fixed-bed reaction is carried out using a pelletized version of a catalyst similar to that described in Example 5. The reaction is performed in an autoclave type reactor in which the catalyst is contained in a perforated, closed-ended tube known as a thimble and is in contact with the reaction medium. The reaction is carried out at about 250°-275° C., and about 2000-5000 psig of hydrogen.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for preparing a catalyst comprising the oxides of copper or zinc and at least one additional metal which comprises the steps of
   (A) simultaneously and separately adding to a first vessel, (1) a first aqueous solution comprising a copper or zinc salt; and (2) a second aqueous solution comprising a soluble base, provided that either (i) the first or second solutions also contains a soluble salt of at least one second metal selected from chromium, molybdenum, tungsten or vanadium, or (ii) if the first or second solutions do not contain a soluble salt of at least one of the second metals, (3) a third aqueous solution comprising a soluble salt of at least one of said second metal is added simultaneously to the first vessel, whereby an aqueous slurry of an insoluble solid is formed in the first vessel;
   (B) advancing at least a portion of the aqueous slurry from the first vessel to a second vessel;
   (C) recovering the solids from the aqueous slurry in the second vessel; and
   (D) calcining the recovered solids wherein the average particle diameter of the calcined solids is from about 6 to about 20 microns; the particle surface area is from about 20 to about 70 m$^2$/g; the pore volume of pores having diameters in the range up to 120 Å is from about 5 to about 45%, in the range of about 120 to about 350 Å is from about 40 to about 80%, and in the range of about 350 to about 1000 Å is from about 10 to about 40% of the total pore volume.

2. The process of claim 1 wherein water also is added simultaneously to the first vessel in step (A).

3. The process of claim 1 wherein a water-soluble salt of at least one promoter metal selected from the group consisting of manganese, barium, zinc, nickel, cobalt, cadmium, iron, calcium, magnesium, and any combination thereof is included in either
   (a) the first aqueous solution, or
   (b) in the third aqueous solution if utilized, or
   (c) is added simultaneously to the first vessel in step (A) as a fourth aqueous solution, provided that the promoter metal is not zinc if the first aqueous solution contains a zinc salt.

4. The process of claim 1 wherein the soluble second metal salt is included in the first aqueous solution.

5. The process of claim 3 wherein the salt of the promoter metal is included in the first aqueous solution.

6. The process of claim 3 wherein the first aqueous solution comprises the soluble salts of copper, chromium and the promoter metal.

7. The process of claim 1 wherein the soluble base in the second aqueous solution is ammonium hydroxide.

8. The process of claim 3 wherein the promoter metal is manganese or barium.

9. A process for preparing a catalyst comprising the oxides of copper and chromium which comprises the steps of
   (A) simultaneously and continuously adding to a first vessel: water; a first aqueous solution comprising soluble salts of copper, chromium, and a promoter metal selected from the group consisting of manganese, barium, zinc, nickel, cobalt, cadmium, iron and any combination thereof; and a second aqueous solution comprising a soluble base, to form an aqueous slurry of an insoluble solid in the first vessel;
   (B) continuously advancing at least a portion of the aqueous slurry from the first vessel to the second vessel;
   (C) recovering at least some of the solid from the slurry in the second vessel; and
   (D) calcining the recovered solid wherein the average particle diameter of the calcined solid is from about 6 to about 20 microns; the particle surface area is from about 20 to about 70 m$^2$/g; the pore volume of pores having diameters in the range up to 120 Å is from about 5 to about 45%, in the range of about 120 to about 350 Å is from about 40 to about 80%, and in the range of about 350 to about 1000 Å is from about 10 to about 40% of the total pore volume.

10. The process of claim 9 wherein the first aqueous solution contains from about 1 up to about 15% by weight of the promoter metal based on the total weight of metals present in the solution.

11. The process of claim 9 wherein the promoter metal is manganese or barium.

12. The process of claim 9 wherein the atomic ratio of copper:chromium in the first aqueous solution is about 1:1.

13. The process of claim 10 wherein the first aqueous solution contains from about 3 to about 10% of manganese based on the total weight of metals present in the solution.

14. The process of claim 9 wherein the soluble base is ammonium hydroxide.

15. The process of claim 9 wherein the aqueous solution of soluble base is added at a rate sufficient to maintain the pH of the aqueous slurry in the first vessel at between about 5 and about 6.5.

16. A process for preparing a catalyst comprising the oxides of copper, chromium and manganese which comprises the steps of (A) simultaneously and continuously adding a first aqueous solution comprising water-soluble salts of copper, chromium and manganese to a first vessel while separately and continuously adding water and a second aqueous solution comprising a soluble base to form an aqueous slurry of insoluble solids in the first vessel;

(B) continuously advancing at least a portion of the aqueous slurry from the first vessel to a second vessel;

(C) continuously recovering at least some of the solids from the slurry in the second vessel; and (D) calcining the solids recovered in step (C) wherein the average particle diameter of the calcined solids is from about 6 to about 20 microns; the particle surface area is from about 20 to about 70 m$^2$/g; the pore volume of pores having diameters in the range up to 120 Å is from about 5 to about 45%, in the range of about 120 to about 350 Å is from about 40 to about 80%, and in the range of about 350 to about 1000 Å is from about 10 to 40% of the total pore volume.

17. The process of claim 16 wherein the atomic ratio of copper to chromium in the first aqueous solution is about 1:1.

18. The process of claim 16 wherein the soluble base in the second aqueous solution is ammonium hydroxide.

19. The process of claim 16 wherein the first aqueous solution contains from about 1 to about 15% by weight of manganese based on the total weight of metals present in the first solution.

20. A catalyst in powdered form comprising a major amount of the oxides of a first metal selected from the group of copper or zinc and a second metal selected from chromium, molybdenum, tungsten and vanadium, and, optionally, a minor amount of the oxide of a promoter metal selected from the group consisting of manganese, barium, zinc, nickel, cobalt, cadmium, iron and any combination thereof, provided that promoter metal is not zinc if the first metal is zinc, and wherein the average particle diameter of the powder is from about 6 to about 20 microns; the particle surface area is from about 20 to about 70 m$^2$/g; the pore volume of pores having diameters in the range up to 120 Å is from about 5 to about 45%, in the range of about 120 to about 350 Å is from about 40 to about 80%, and in the range of about 350 to about 1000 Å is from about 10 to about 40% of the total pore volume.

21. The catalyst of claim 20 wherein the first metal is copper.

22. The catalyst of claim 20 containing up to about 15% by weight of at least one oxide of at least one promoter metal.

23. The catalyst of claim 20 wherein the promoter metal is manganese.

24. The catalyst of claim 20 wherein the second metal is chromium.

25. The catalyst of claim 24 wherein the packed bulk density is from about 0.8 to about 1.3 g/cc.

26. The catalyst of claim 25 wherein the atomic ratio of copper:chromium is about 1:1.

27. The catalyst of claim 23 containing from 1 to about 15% by weight of manganese.

28. The catalyst of claim 20 wherein the surface area of the particles is in the range of from about 25 to about 65 m$^2$/g.

29. The catalyst of claim 20 wherein the average particle diameter of the powder is from about 6 to about 12 microns.

30. The catalyst of claim 20 wherein the particles are all below 25 microns in diameter, at least about 80% are below 15 microns, about 50% are below about 8 microns and about 0% are below 2 microns.

31. A catalyst prepared in accordance with the process of claim 1.

32. A catalyst prepared in accordance with the process of claim 16.

* * * * *